(12) United States Patent
Hagen et al.

(10) Patent No.: US 8,073,225 B2
(45) Date of Patent: Dec. 6, 2011

(54) METHOD AND DEVICE FOR CONTROLLING IMAGE DATA ACQUISITION AND IMAGE RECONSTRUCTION

(75) Inventors: Ulrich Hagen, Trailsdorf (DE); Oliver Heid, Gunzenhausen (DE); Thomas Kluge, Hirschaid (DE); Markus Vester, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 1397 days.

(21) Appl. No.: 11/450,631

(22) Filed: Jun. 9, 2006

(65) Prior Publication Data

US 2006/0285735 A1    Dec. 21, 2006

(30) Foreign Application Priority Data

Jun. 10, 2005  (DE) .................. 10 2005 026 890

(51) Int. Cl.
*G06K 9/00* (2006.01)
(52) U.S. Cl. ......... 382/131; 382/128; 382/304; 345/629
(58) Field of Classification Search .................. 382/128, 382/131; 345/629; 717/144, 132; 703/115; 714/38
See application file for complete search history.

(56) References Cited

U.S. PATENT DOCUMENTS

| | | | |
|---|---|---|---|
| 6,567,114 B2 * | 5/2003 | Takahashi et al. | 348/71 |
| 7,076,416 B2 * | 7/2006 | Chen et al. | 703/15 |
| 7,243,216 B1 * | 7/2007 | Oliver et al. | 712/218 |
| 2002/0188890 A1 * | 12/2002 | Shupps et al. | 714/38 |
| 2004/0122790 A1 * | 6/2004 | Walker et al. | 707/1 |
| 2004/0223003 A1 * | 11/2004 | Heirich et al. | 345/629 |
| 2006/0048113 A1 * | 3/2006 | Ozone et al. | 717/144 |
| 2008/0132778 A1 * | 6/2008 | Shankaranarayanan et al. | 600/413 |
| 2009/0251141 A1 * | 10/2009 | Baumgartl et al. | 324/307 |

OTHER PUBLICATIONS

"Efficient Visualization of Large Medical Image Datasets on Standard PC Hardware," Pekar et al, Joint Eurographics-IEEE TCVG Symposium on Visualization (2003) pp. 135-140.

* cited by examiner

*Primary Examiner* — Anand Bhatnagar
*Assistant Examiner* — Xuemei Chen
(74) *Attorney, Agent, or Firm* — Schiff Hardin LLP

(57) ABSTRACT

In a method and a device for optimization of a combined system for the acquisition of magnetic resonance tomographic measurement data and an image reconstruction process, the image reconstruction process is already executed during the acquisition of the measurement data, by the calculation process being deconstructed into calculation packets, and rules are defined that establish which requirements must be met for the execution of the respective calculation packet. The calculation process is reorganized into a workflow structure based on the calculation packets and the rules. The calculation process is controlled using the generated workflow structure synchronized to the acquisition process. The rules entirely describe the calculation process, i.e. inclusive of all calculation packets and their logical dependencies. The stability of the calculation process is thus entirely independent of the chronological order of the measurement data acquisition.

15 Claims, 7 Drawing Sheets

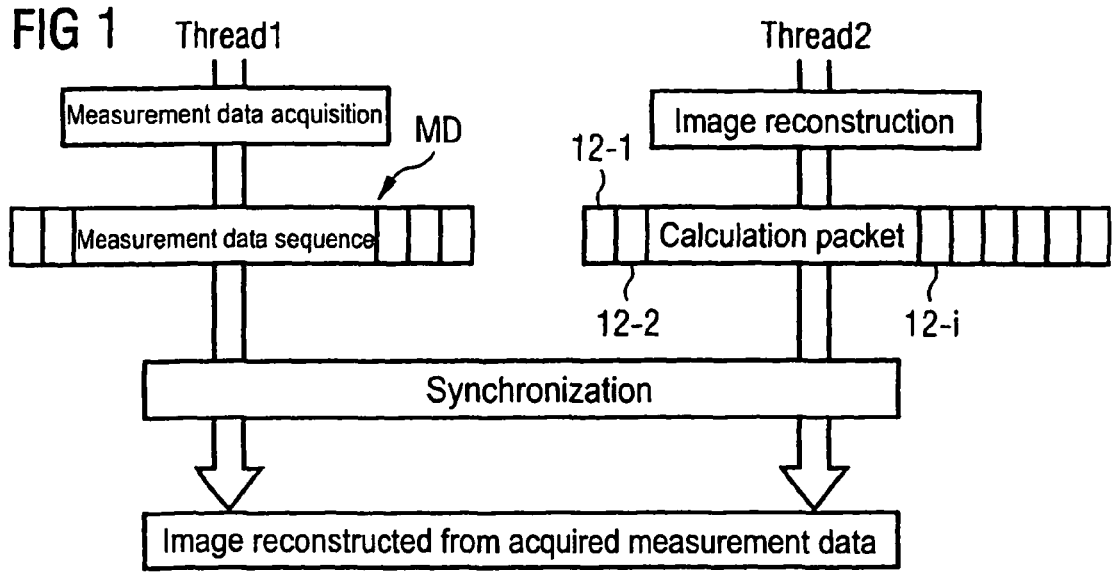
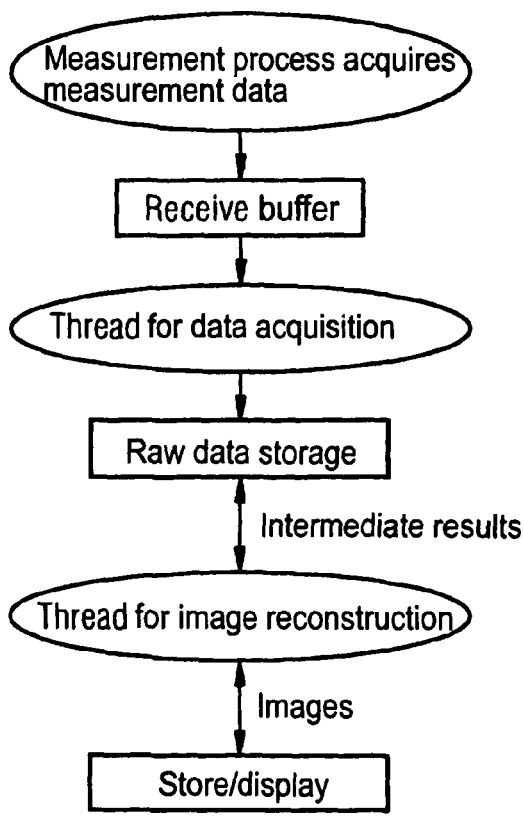

Slice slc, Channel cha

Slice slc, Channel cha

METHOD AND DEVICE FOR CONTROLLING IMAGE DATA ACQUISITION AND IMAGE RECONSTRUCTION

BACKGROUND OF THE INVENTION

1. Field of the Invention

The present invention is in the field of image processing, particularly in the field of image reconstruction, such as reconstructing an image from data acquired with a magnetic resonance apparatus.

2. Description of the Prior Art

Magnetic resonance tomography (MRT) is a modern imaging modality wherein a static, basic magnetic field aligns the nuclear spins of selected nuclei in an examination subject that were previously randomly oriented. Radiofrequency energy is irradiated into the examination subject, causing the spins to "tip" and emit magnetic resonance signals as they return to their equilibrium state. Using these magnetic resonance signals, slice exposures can be generated etc. Slice exposures can be generated of nearly every body part at any angle and in any direction. The data exist in digital form and can be processed into meaningful images by the use of computer systems. The average examination time is approximately 20 to 60 minutes. Due to the physical principle for acquiring the measurement data, the slice images must be processed into a three-dimensional representation, so it is necessary to process a large amount of digital data. This places high performance and storage demands on the processing components.

Imaging methods are used not only in the field of diagnostics but also are used to supervise or conduct interventional or surgical procedures, wherein the imaging can occur online (in real time). It is thereby necessary to achieve as optimal a performance as possible, both as to the acquisition system for the measurement data and as to the calculation process for the measurement data, in order to be able to keep the risks for the patient as minimal as possible. For example, MR-controlled procedures exist in the field of interventional radiology such as biopsies, interventions for liver tumors, treatment of osseous lesions, and percutaneous vertebral biopsies particularly in interventional radiology it is an indispensable requirement that an optimized image processing and imaging can be ensured in real time in order to be able to plan the precision of the procedure and in order to be able to ensure the highest patient safety.

Methods for efficiency improvement are known. The article "Efficiency visualization of large medical image Datasets on standard PC hardware", Proceedings of the symposium on Data visualization, ACM International Conference Proceeding Series; Vol. 40, pages 135-140 from the year 2003 by Pekar, V. et al. discloses a hardware-based approach in order to be able to efficiently display medical image data. Here an algorithm is proposed that is applied to already-acquired medical image data and is intended to enable a more efficient visualization of the image data in that a memory caching strategy is modified. The algorithm disclosed therein deconstructs (dismantles) the data set such that it is adapted to the size of the cache. This is also achieved by a parallel processing. This article, however, does not disclose a suitable, interdependent nesting (interleaving) strategy for a combined acquisition and calculation process in which the later calculation process is separated such that an optimal result can be achieved with regard to the sequence of the data acquisition.

Moreover, U.S. Application Publication 2004/0223003 A1 discloses an image processing method and an associated image generator in which an overall image is deconstructed into image parts that are respectively processed in parallel-executed threads with rendering units and merging units being provided in the threads. The processing speed for display of an image data set in fact can be increased with the approach proposed in this publication, but there is no description of a combined acquisition and calculation process wherein the calculation process is structured so as to be optimal for the acquisition process, particularly the sequence of the acquired image data.

A basic factor of importance is the computer-controlled acquisition and processing of the image data. It is necessary to ensure that degradations or limitations due to the imaging do not occur. Furthermore, it is important to control the image data acquisition (via the modality of the magnetic resonance tomography apparatus in the example above), particularly the scan control, such that the image reconstruction and image evaluation based thereon can ensue in a time-optimized manner.

A magnetic resonance tomography system typically includes a basic field magnet that generates a static magnetic field in order to polarize the atomic nuclei in the body or body part to be examined. A transmitter for radio-frequency pulses and corresponding receivers are used for exciting the MR signal and the acquisition thereof. A system computer controls the measurement data acquisition and is used for the administration of measurement data as well, plus the further processing of the data or and for the reconstruction of images from the acquired measurement data. Since the further calculation of image data and the reconstruction of images are based on the acquisition of the respective measurement data, it is necessary for specific ranges of measurement data to be acquired in a temporally preliminary (advance) phase in order to later be processed for the reconstruction. This, however, would lead to unacceptable delays if the measurement process would have to be completely executed before the subsequent reconstruction can be started. A decisive point for the performance (quality) of such systems is the temporal meshing between the acquisition process and the subsequent calculation process.

A combined acquisition and calculation of measurement data are known, but these known solutions are based on a pipeline-like, serial processing of input data. The image data are acquired in a specific manner and in a specific order (i.e. in a specific measurement sequence). This measurement sequence, thus the order of the acquisition of the measurement data, typically can be configured by controlling the hardware of the MR scanner in a specific manner. The calculation process thus is disadvantageously not flexibly adaptable. In particular, conventionally it has not been possible to change the configuration of the calculation process. Previous systems are thus dependent on an explicit and additional synchronization between the reconstruction process and the acquisition process and/or on a predetermined temporal measurement order. The accuracy (and therewith the performance) of the overall system thus disadvantageously depends on an additional task, namely the explicit synchronization and/or the retention of the necessary measurement order. If this task can only be imperfectly executed, the result of the image reconstruction can likewise be imperfect or even unusable (from a qualitative and/or temporal point of view).

Moreover, there are multiple calculation processes (in particular reconstruction processes) that can be used in this context. It has proven to be disadvantageous that there is no uniform and/or no complete description of these calculation processes.

Therefore it has not been conventionally possible to adapt the calculation processes to the requirements of the acquisition process. By contrast, in specific situations the acquisition process (in particular the order of the measurement data acquisition) would have to be adapted to the requirements of the reconstruction process. This is only possible, however, in a very limited manner since (particularly in MR image data acquisition) there are a number of physical requirements that must be adhered to and that thus limit the configuration freedom. The possibilities for influencing and the interlocking of the two processes are therefore sub-optimal in the known systems.

SUMMARY OF THE INVENTION

An object of the present invention is to provide a method and device that allow the performance, the stability and/or the flexibility of a combined acquisition and calculation process to be improved and that allow an efficient use of the time that is required for the calculation or for the calculation process. Moreover, the logical dependencies and the parallel relation of all underlying possible and usable calculation processes should be described simply and in a standardized manner.

This object is achieved in accordance with the invention by a method for optimization of a combined acquisition and calculation process wherein the acquisition process is designated to acquire measurement data and wherein the calculation process is designated to execute further calculations on the acquired measurement data in parallel with the acquisition process and wherein the data exchange between the acquisition process and the calculation process ensue via a suitable interface. The inventive method includes the steps of:

deconstruction of at least the calculation process into calculation packets, specification of a rule or set of rules for each calculation packet, that establish which logical dependencies exist between the calculation packets and in particular which requirements must be fulfilled and/or which and how many measurement data must already be acquired for the execution of the respective calculation packet, restructuring the calculation process into a workflow structure based on the calculation packets and on their rules, and control of the calculation process using the workflow structure, so that the respective calculation packet is automatically executed at the earliest possible point in time.

In a preferred embodiment of the invention, the measurement data are magnetic resonance tomographic measurement data that are processed into images with a reconstruction process. Here the calculation process is thus the process of the reconstruction or the image generation. However, it is possible to likewise apply the present invention to other measurement data and/or to other processes that include further processing of measurement data, allowing the further processing to ensue in parallel and synchronized for acquisition of the measurement data. Examples of acquisition of process data and the subsequent process control are synchronization of the acquisition of synchronization of test and laboratory data and the subsequent evaluation of these data, and synchronization of the acquisition of system parameters and the subsequent usage of these data for the purposes of configuration or diagnosis.

Moreover, the acquisition process does not necessarily have to be designed for the acquisition of measurement data. Acquisition modalities of the data such as, for example, the importation of data from a storage or from a databank are likewise conceivable. The term "measurement data" as used herein encompasses input data of any type.

Known systems in the field of combined MR measurement data acquisition and image calculation applied merely to implementation of optimally fast algorithms for calculation of a result (thus algorithms for the calculation process). However, this procedure has a natural limitation with regard to the performance since the bottleneck lies in the combination of the two processes. The reconstruction process requires that specific measurement data have already been acquired and thus can be the basis for a further calculation. It has proven to be reasonable to superimpose an acquisition and calculation time that is designed to be approximately similar in length.

A significant advantage of the present invention lies in the approach of parallelizing and synchronizing the MR data acquisition and the MR image calculation, such that optimally many tasks of the reconstruction process can already be executed in the measurement data acquisition.

This is inventively achieved by deconstructing both processes—the measurement data acquisition process and the image calculation process (or the reconstruction process in the example above)—into smaller sub-processes, into what are known as calculation packets. Moreover, it is established which requirements must be fulfilled so that the respective calculation packet can be executed. This is typically established by parameterized rules which embody all logical dependencies. Temporal dependencies are not considered here. This has the advantage that the method is flexible and independent of the chronological acquisition sequence.

The rules completely describe the calculation process, i.e. inclusive of all calculation packets and their logical dependencies. The stability of the calculation process is thereby completely independent of the chronological order of the measurement data acquisition.

The order of the measurement data acquisition is thus arbitrary in the inventive procedure. The processing of individual calculation packets is temporally varied when the order of the measurement data acquisition varies. The calculation thus can be controlled independently of the acquisition.

According to the invention, the method organizes itself. It can advantageously be ensured that the method terminates as quickly as possible. Using the adaptively-generated workflow structure, all calculations can be implemented that are possible at this point in time (or, respectively, for the previously-acquired data). The calculation process thus is not dependent on a chronological acquisition order.

The following are examples of requirements that must be fulfilled for the execution of a calculation packet:

a specific group of measurement data must be acquired;

another calculation packet must already have been executed;

results of other instances must exist and/or the technical resources for the execution of the respective calculation packet must be present.

By deconstructing the combined acquisition and calculation process into smaller units and generating a workflow structure for the calculation process (which already implies a synchronization between the two processes) in accordance with the invention, it is possible in an advantageous manner to utilize modern computer architectures and (for example) 64-bit multiprocessor platforms such that a maximal degree of parallelization can be achieved. Advantages of the modern computer architectures thus can be efficiently utilized in that multiple sub-tasks can be executed in parallel threads of a multiprocessor system. In the preferred embodiment, the method is therefore designed for a multiprocessor system. Each calculation process or a group of calculation processes is divided into a number of threads running in parallel. A modern computer architecture thus can be efficiently utilized in that the generated workflow structure can be adapted to the number of the available CPUs. Alternative solutions are based on a single processor machine, with which the basic idea of the present invention can also be applied. Given a single processor machine, it is also in particular possible to choose optimally many calculation tasks in the measurement. The method thus can be flexibly adapted to the respective computer architecture.

A number of possible and usable algorithms exist in the field of MR reconstruction. The present solution is not limited to any specific algorithm and can be applied to any calculation processes in which a data structure is provided in which the calculation process is respectively restructured. A specific and optimally-designed notation can be provided for the description of the image calculation during the image acquisition.

The inventive method is typically subdivided into two temporal segments:
1. A preparation phase in which the calculation process is deconstructed into calculation packets, in that for each calculation packet it is specified which requirements for its execution must be fulfilled or which logical dependencies the respective calculation packet has, and in which the calculation process is transformed into a new structure (namely into a workflow structure) that is based on the defined calculation packets and on the defined dependencies and/or requirements.
2. An execution phase: this execution phase serves for execution of the acquisition and the calculation using the generated workflow structure and for exchange of the respective data. Optimally many calculation packets are executed in parallel during the acquisition process, in particular during the scanning of the MRT apparatus.

Specific events that should initiate a display of the intermediate results can be defined in the preparation phase. For example, when an MRT scan of multiple body parts of a patient is to be executed, it can be set to cause an intermediate result to be displayed after conclusion of the acquisition of the measurement data for one respective body part and/or after reconstruction of the image for a body part.

The preparation phase is typically before the execution phase from a temporal point of view, but this is not mandatory. It is also possible to merge both phases. Rules can also be additionally provided at a later point in time. This distinctly increases the flexibility of the inventive solution.

The preparation phase can include a fixed part and a dynamic part. Rules (subsequently-supplied) can be defined in the dynamic part. Here it is possible to configure further settings.

Furthermore it is possible to define priorities. All calculation packets that, for example, generate a specific result or result object can be designated as highest priority while other packets have a subordinate priority. Here the calculation packets are selectively additionally grouped and processed with regard to their priority.

Due to the fact that the preparation phase takes place in advance, it is possible to free the CPU from additional tasks in that all definition and specification tasks can already be completed in advance. In the preferred embodiment, the parameterized rule set for the calculation process is generated in the framework of the development process for the calculation process. The developer of the reconstruction process will typically define the rule set with regard to the measurement data acquisition. However, in contrast to the prior art the method is robust with regard to a suboptimally-designed acquisition of the measurement data.

In other words, the calculation process (deconstructed into individual calculation packets) is inventively transformed into a workflow structure. In this workflow structure the specifications for a synchronization with the acquisition process are implicitly regulated. Two synchronization points are typically defined for each calculation packet. All logical dependencies of the respective packet (thus in particular on which other events or packets the respective packet is dependent and which other events or packets depend on the respective packet) are defined in a synchronization point.

A calculation packet can in principle only be executed when all logical requirements are fulfilled, i.e. when specific events have occurred. The successful execution of a calculation process can thereby be such an event for other calculation processes. Other examples for events cited in the preceding are, for example, the acquisition of measurement data, the pre-processing of the acquired measurement data or the processing of "adjacent" measurement data. The requirements that must be fulfilled for the execution of the respective calculation packet can include such an event; however, they can also comprise an arbitrary combination of such events.

According to the invention, a mechanism is provided that blocks a calculation packet from its execution until all requirements are fulfilled and that can initiate the execution of other calculation packets or can exclude the other calculation packets from the blocking. This mechanism is formed by the synchronization points in the preferred embodiment.

In this embodiment, there are in principle two categories of synchronization points:
1. Blocker: monitors whether all events have occurred that have been defined as a requirement for the respective calculation packet. As long as all requirements have not been fulfilled, the blocker blocks the packet from its execution.
2. Collector: this synchronization point starts the respective execution of the calculation packet and/or registers this from the point of view of the respective calculation packet.

A specific synchronization point is typically simultaneously a collector for specific calculation packets and a blocker for specific other calculation packets.

There are three excellent synchronization points, namely the data acquisition point (which represents the direct dependency on measurement data), a blocker unblocked from the outset (which allows it to define work packets that are dependent on nothing) and exactly one collector per desired calculation result (which specifies whether the result was correctly calculated).

The interdependencies between the individual calculation packets are specified by parameterized rules in the preferred embodiment. The individual calculation packets and their logical dependencies are defined in the rules. Each rule can be applied multiple times; the number of the repetitions is thereby a component of the rule. The multiple repetitions must be resolved. This is achieved by a repetition index.

In the preferred embodiment of the invention, it is possible to connect external programs via a corresponding interface, which external programs are, for example, designed for the representation and display of the workflow structure. An input file that includes the parameterized rules is then mapped in a graphical representation, for example in a positional graph or in a table.

The dependencies between the individual calculation packets are shown in the generated data structure together with the synchronization points. The graph can include multiple root nodes and, in principle, has only one leaf (namely the result). The links are the processes to be executed (the calculation tasks) and the nodes are the synchronization points.

This graphical representation can be output in order to check the restructuring of the calculation process into the workflow structure for correctness. For example, if the graph has multiple leaves, the process has been incorrectly restructured since only one end result can exist.

The above object thus also is achieved by a data structure used to implement the above-described method. This notation is complete and includes all calculation packets and all dependencies.

This object is achieved in accordance with the invention by a data structure for a calculation process for use in a method described above that includes a number of calculation packets into which the calculation process is deconstructed, two synchronization points for each individual calculation packet, with which it is defined which requirements or which logical dependencies the calculation packet has, and an association (link) between one calculation packet and the two synchronization points.

An association relation is created only in the event that an association exists. Given an initial measurement data acquisition and given the termination of the last activity of the calculation process, in particular after the storage of the reconstructed image, such an association is only necessary in part or is no longer necessary. With this data structure it is possible to immediately, automatically and separately detect for each calculation packet which requirements must be fulfilled for its processing.

With the inventive data structure it is possible to uniformly describe the most different reconstruction algorithms in different complexity in a standardized manner, and to use this description for the parallelization and synchronization with the acquisition process.

A particular advantage of the inventive solution is that the method is dynamically configurable and can be adaptively matched to the respective context conditions, by recording possible changes in the workflow with regard to the acquisition and/or the calculation of the measurement data. It is in particular possible to alter the measurement sequence, thus the order of the acquisition of the measurement data. This typically ensues via a corresponding user interface. Moreover, it is possible to select another algorithm as the basis for the calculation process and/or to vary other parameters and settings of the combined acquisition and calculation process. The inventive solution is thus independent in principle from the current organization of the calculation packets, from the acquisition process and/or from the currently-selected workflow.

According to the invention it is possible to control the calculation process independent from the measurement data acquisition (the order, speed and/or further parameters). The workflow structure provides a number of threads running in parallel that respective execute individual calculation packets. The workflow structure is thereby designed such that the calculation packet whose requirements are fulfilled (in particular whose measurement data are acquired) is automatically executed. It is therewith ensured that the chronological execution of the individual sub-tasks of the calculation process is automatically optimized such that: a maximum portion of calculation work can already have occurred during the acquisition of the measurement data.

The restructuring of the calculation process includes a synchronization between measurement data acquisition and measurement data calculation or construction, that is limited to only the identification of the data packet. A significant advantage thereof is that the inventive method needs no further modules for an external temporal synchronization, and thus is more stable and less error-prone. Moreover, the method is self-organizing. This also contributes to the distinct reduction of the proclivity for error (error rate) since the method can run automatically and no errors (possibly due to incorrect user interactions) can arise.

In a preferred embodiment, a buffer storage is used in which raw data of the measurement data acquisition are stored. Moreover, it is possible to store intermediate results of the reconstruction process therein. As soon as a set of measurement data has been acquired, it is cached in the buffer storage. The measurement data are then read out from this cache when they are required by the respective calculation packet. Moreover, a storage monitoring mechanism is provided that makes sure that the acquisition process does not pump further raw data into the storage in the event that this is full because the calculation process is occupied and can read and process no further measurement data at the time.

In a more complex embodiment of the invention, it is not necessary to constantly maintain the acquisition process in its original form. The order of the measurement data acquisition can be modified. The acquisition process is controlled for this purpose such that the measurement data that must be processed first in the reconstruction process are acquired earliest. In this case, the workflow structure is evaluated together with the synchronization points, such that the calculation packets respectively request their necessary measurement data as needed and initiate a corresponding measurement process for that data. This has the advantage that less raw data must be cached in the buffer storage, and contributes to a further performance improvement.

Generally, the control of the calculation process automatically ensues using the inventively-generated workflow structure. This includes the automatic readout of required measurement data sets from the buffer storage. It is thus ensured that all calculation packets (thus calculation sub-tasks) are automatically executed that can be executed at the respective point in time (in particular with regard to the measurement data acquisition). In an embodiment of the invention, all or selected method steps of the method described in the preceding are executed automatically.

The above object also is achieved in accordance with the invention by a device that implements the above-described method. The advantages, features, alternative embodiments mentioned in the preceding in connection with the inventive method are correspondingly applicable to the inventive device.

The embodiments of the inventive method described in the preceding also can be implemented by a computer program product embodying program code stored in a computer-readable medium.

Moreover, it is possible for individual components of the method described in the preceding to be executed in one commercial unit, and the remaining components can be executed in another commercial unit, i.e. a distributed system.

The above object also is achieved in accordance with the present invention by a product (enhancement card or module) for optimization of an acquisition and calculation unit, in particular of an image data acquisition and calculation unit, wherein the unit acquires measurement data and makes calculations based on the acquired measurement data. The inventive product allows further measurement data to be acquired by the unit in parallel with the execution of the calculations, whereby an interface is provided via which the acquisition functions and the calculation functions. The product has a number of calculation modules that are designated to execute the functions (deconstructed into calculation packets) of the calculation and which can be divided into various threads, at least one synchronization unit that, using rules, establishes for each calculation packet which logical dependencies on other packets exist, a data structure for the workflow of the calculation packets of the calculation unit, based on the synchronization unit, and at least one control unit that controls the execution of the calculation unit using the generated data structure, so that a respective calculation packet is automatically executed at the earliest possible point in time as soon as its synchronization unit initiates such execution.

The product in accordance with the present invention can embody all of the different versions and modifications described above in connection with the inventive method.

DESCRIPTION OF THE DRAWINGS

FIG. 1 is an overview of a measurement data acquisition and image reconstruction process according to a preferred embodiment of the invention.

FIG. 2 illustrates data flow according to a preferred embodiment of the invention.

DESCRIPTION OF THE PREFERRED EMBODIMENTS

Figure 3:
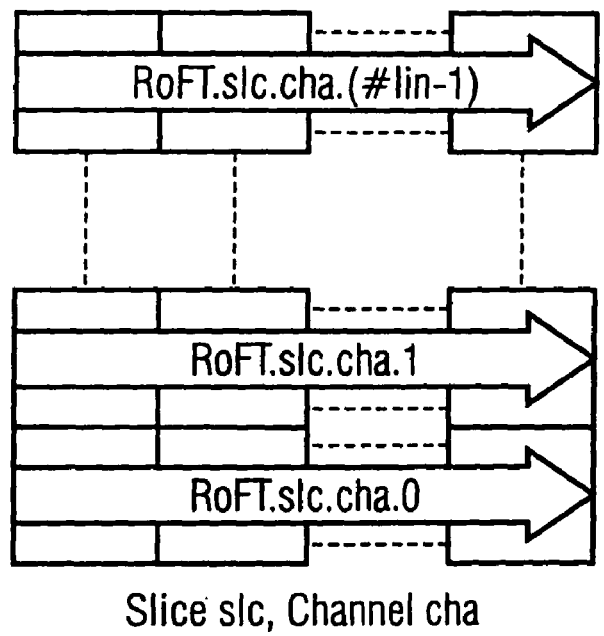
FIG. 3 shows an exemplary application of the inventive method to the readout of a Fourier-transformed representation.
Figure 4:
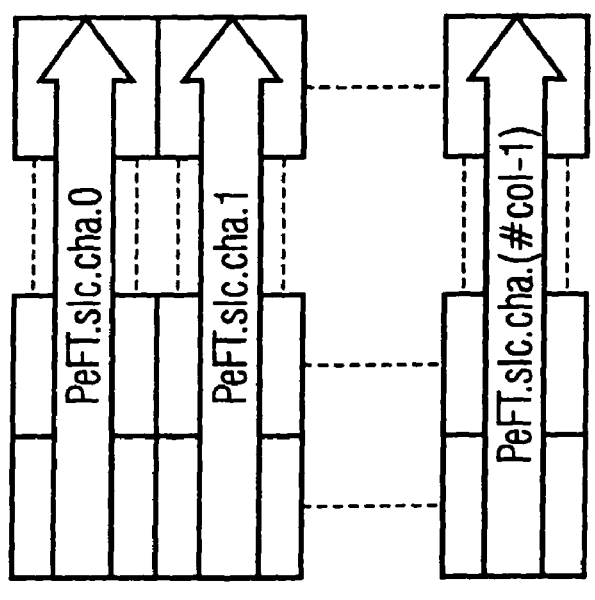
FIG. 4 shows an exemplary application of the inventive method to the execution of a phase-encoded Fourier transformation.
Figure 5:
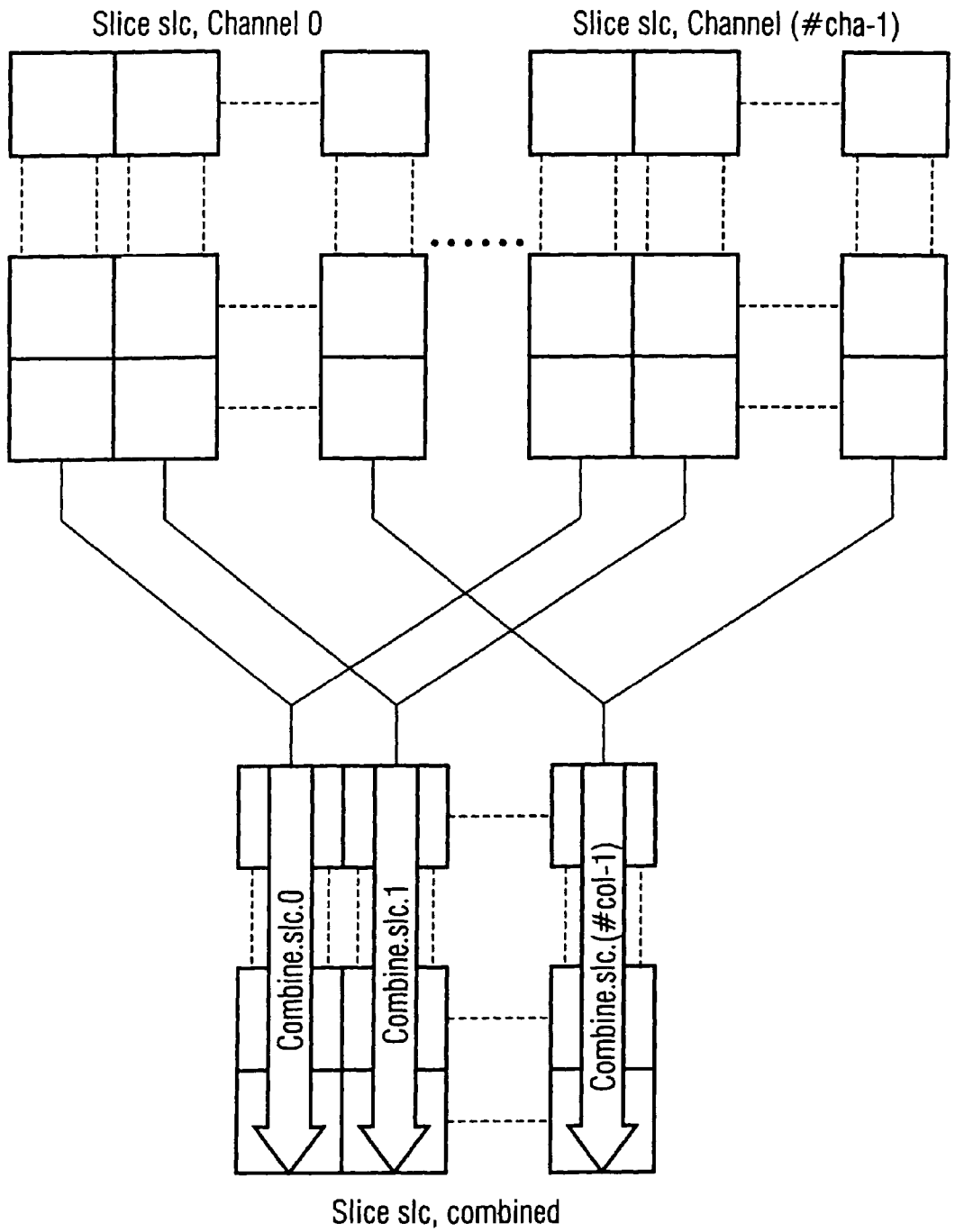
FIG. 5 shows an exemplary application of the inventive method to a combination of the preceding calculations.
Figure 6:
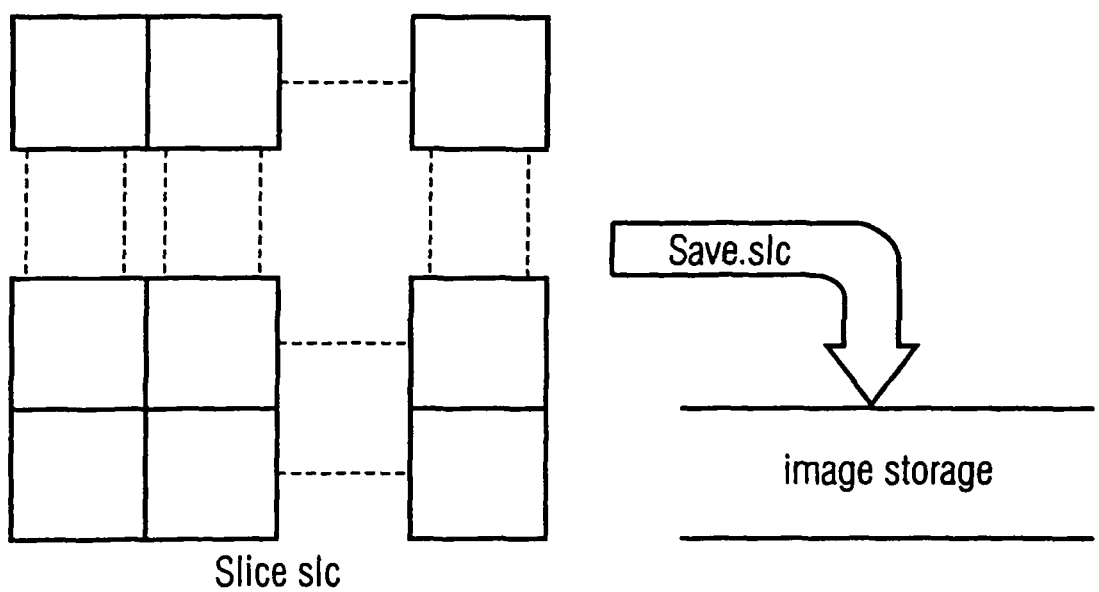
FIG. 6 shows an exemplary application of the inventive method to the storage of a calculated image.

The primary field of application of the present invention is the acquisition of measurement data in a magnetic resonance imaging apparatus, thus MRT data, and the image reconstruction process therefor. In principle, however, the measurement data acquisition process is not limited to data of a magnetic resonance tomography apparatus, but rather can likewise be data of other modalities, for example CT data, PET data, etc. The calculation process is likewise not limited to an image reconstruction process, but rather can be applied in all types of post-processing of acquired measurement data.

As shown in the overview in FIG. 1, the preferred embodiment is a combined measurement data acquisition and image reconstruction process. Two threads are thereby normally provided that run in parallel.

The image reconstruction process is inventively deconstructed into a number of calculation packets 12-1, 12-2, ... , 12-n. Dependent on which measurement data have already been acquired at this point in time, the calculation packet 12-i whose requirements are fulfilled is executed. In particular all measurement data MD that must be processed by the respective calculation packet 12-i must be acquired. This is ensured in accordance with the invention by a synchronization unit 14. The control unit 16 undertakes the synchronization and parallelization between the two processes and, if applicable, further control tasks. The respective units communicate via corresponding interfaces, and in particular the acquisition unit 10 and the calculation unit 12 interact via the interface 11.

In general, with the method presented herein it is ensured that all calculation tasks can be executed that are executable at this point in time, i.e. in particular whose measurement data have been acquired up to this point in time. It is thus ensured that the combined measurement data acquisition and image reconstruction process generates a reconstructed image as fast as possible.

As shown in FIG. 2, the measurement data MD are normally acquired by a magnetic resonance apparatus (scanner) in a measurement procedure and are written into a reception buffer. The thread for the data acquisition reads these data from the reception buffer and writes the data so acquired into a raw data storage. The thread for the image reconstruction reads the data from the raw data storage and processes these into partial results that can in turn be cached in the raw data storage. As soon as all measurement data MD have been acquired and exist and as soon as all calculation or reconstruction processes (tasks) have been executed, the image or the images can be stored in a storage, or can be shown on a display device.

An inventive data flow architecture enables the calculation process (in particular the image reconstruction) to ensue already during the measurement data acquisition.

In an advantageous manner, the inventive method for optimization of the performance, the stability and the flexibility of a combined acquisition and image reconstruction process is independent of the selection of the respective image reconstruction process. Any reconstruction algorithm can be used here.

The primary workflow is subsequently explained:

The reconstruction process is deconstructed into individual calculation packets 12-i. For each calculation packet 12-i it is thereupon defined which requirements must be fulfilled for the execution of this calculation packet 12-i, in particular which measurement data MD must be acquired. The calculation process is thus converted into a new data structure. This workflow data structure is based on the calculation packets 12-i and their rules and comprises two synchronization points for each calculation packet 12-i. These method steps can be executed in a preparation phase before the execution of the actual measurement and reconstruction process.

The parallelized and synchronized control of the calculation process follows. The calculation process is controlled using the generated workflow structure, independent of the order of the measurement data, acquisition, in that the respective calculation packet whose synchronization point is reached is executed at the earliest possible point in time. This means the calculation packets 12-i whose measurement data MD are present is/are automatically executed.

The inventive parallelization and synchronization of the MR reconstruction process is shown in the following in connection with FIG. 3 through 6. This example concerns the generation of two-dimensional images that have been acquired via multiple acquisition channels. The number of the slice exposures (slices) is abbreviated with "#slc". Lines, columns and channels are respectively abbreviated with "lin", or "col" and "cha".

The data are simultaneously acquired line for line via all channels in a different order with regards to the lines and the slices.

As shown in FIG. 3, each line input signal is supplied to a Fourier transformation. This process is denoted as a "read-out Fourier transform" (readout of a Fourier-transformed representation) and is abbreviated with "RoFT". An RoFT operation is thus necessary for each line of each channel of each slice.

The columns are also supplied to a Fourier transformation. This process is denoted in FIG. 4 with "phase-encode Fourier transform" and is abbreviated with "PeFT". A PeFT operation is necessary for each column of each channel of each slice.

The images of the channels are combined in order to acquire a final image for a slice. This procedure is denoted with "combine". A column is respectively combined with another column. A "combine" process is necessary for each column of each slice. The process of the combination or of the merging is shown as an example in FIG. 5.

The slices are subsequently stored. This process is shown as an example in FIG. 6 as "save" (for storage). A storage operation is necessary for each slice.

In the example just shown, the calculation process is the processing of Fourier-transformed lines and columns for the representation of a two-dimensional image. The actual algorithm or the actual calculation process has been deconstructed into small calculation packets 12-$i$. In the above example, a calculation packet 12-$i$ can pertain to the readout of a Fourier-transformed representation of a line (RoFT), the phase-encoded Fourier transformation (PeFT), the combination and/or the storage processes.

These calculation packets 12-$i$ can be divided among multiple processors of a CPU. The order of the execution of the individual processing packets 12-$i$ is inventively, automatically synchronized with the order of the measurement data acquisition.

It is necessary to define rules in order to describe the primary calculation process in more detail. The rules are parameterized in the preferred embodiment and can be represented according to the following under reference to the example above:
    the RoFT process of a line can only be executed when the measurement data MD are scanned;
    the PeFT process of column can only be executed after all RoFT operations of all lines of the same channel and the same slice have been completed;
    the combination of a specific column can only be executed after all PeFT operations of this column had been completed for all channels of this slice and
    the slice exposure can only be stored after all columns have been combined.

The rules can be shown in the form of the following table:

| Task | Blocker | Collector | Repetitions | Resolved placeholder |
|---|---|---|---|---|
| Save.slc | Combined.slc | Saved.slc | #slc | Slc(i) |
| Combine.slc.col | PeFTed.slc.col | Combined.slc | #slc * #col | Slc(i), col(i) |
| PeFT.slc.col.cha | RoFTed.slc.cha | PeFTed.slc.col | #slc * #col * #cha | Slc(i), col(i), #cha(i) |
| RoFT.slc.lin.cha | Data acquisition | RoFTed.slc.cha | #slc * #lin * #cha | Slc(i), lin(i), cha(i) |

Via these parameterized rules it is possible to define which events must be fulfilled so that specific calculation packets 12-$i$ can be executed. The successful execution of a calculation packet 12-$i$ is, for example, an event for other respective calculation packets 12-$i$. Moreover, the acquisition of measurement data MD that should be processed in the calculation packet 12-$i$ is an example of such an event.

For this purpose, a mechanism is inventively provided that enables a specific calculation packet 12-$i$ to be blocked (and thus remains excluded from the execution) as long as all requirements are not met. Moreover, it is necessary to detect the execution of a calculation packet 12-$i$ and to cancel the blocking of calculation packets 12-$i$. This mechanism is formed by the synchronization points.

In the preferred embodiment, two synchronization points are defined for each calculation packet 12-$i$.

In principle, there are two types of synchronization points:
    points known as blockers and
    points known as collectors.

A synchronization point functions as a blocker when it serves to block (or to exclude) a calculation packet 12-$i$ from being executed in the event that all requirements therefor are not yet met. A synchronization point functions as a collector in the event that it detects or registers the execution of the respective calculation packet 12-$i$.

After the deconstruction of the calculation process into a number of calculation packets 12-$i$ and after the specification of rules for each calculation packet 12-$i$, a data structure can be created (advantageously a data structure in tabular form) that includes the respective calculation packets 12-$i$, the synchronization points and the rules (including the number of the repetitions for these rules). The calculation process thus has been mapped to a set of parameterized rules. The rules designate the calculation packets 12-$i$ and their logical dependencies or their interdependencies.

The calculation process is inventively restructured into a workflow structure. This workflow structure is based on the individual calculation packets and their logical requirements or synchronization points.

Figure 7:
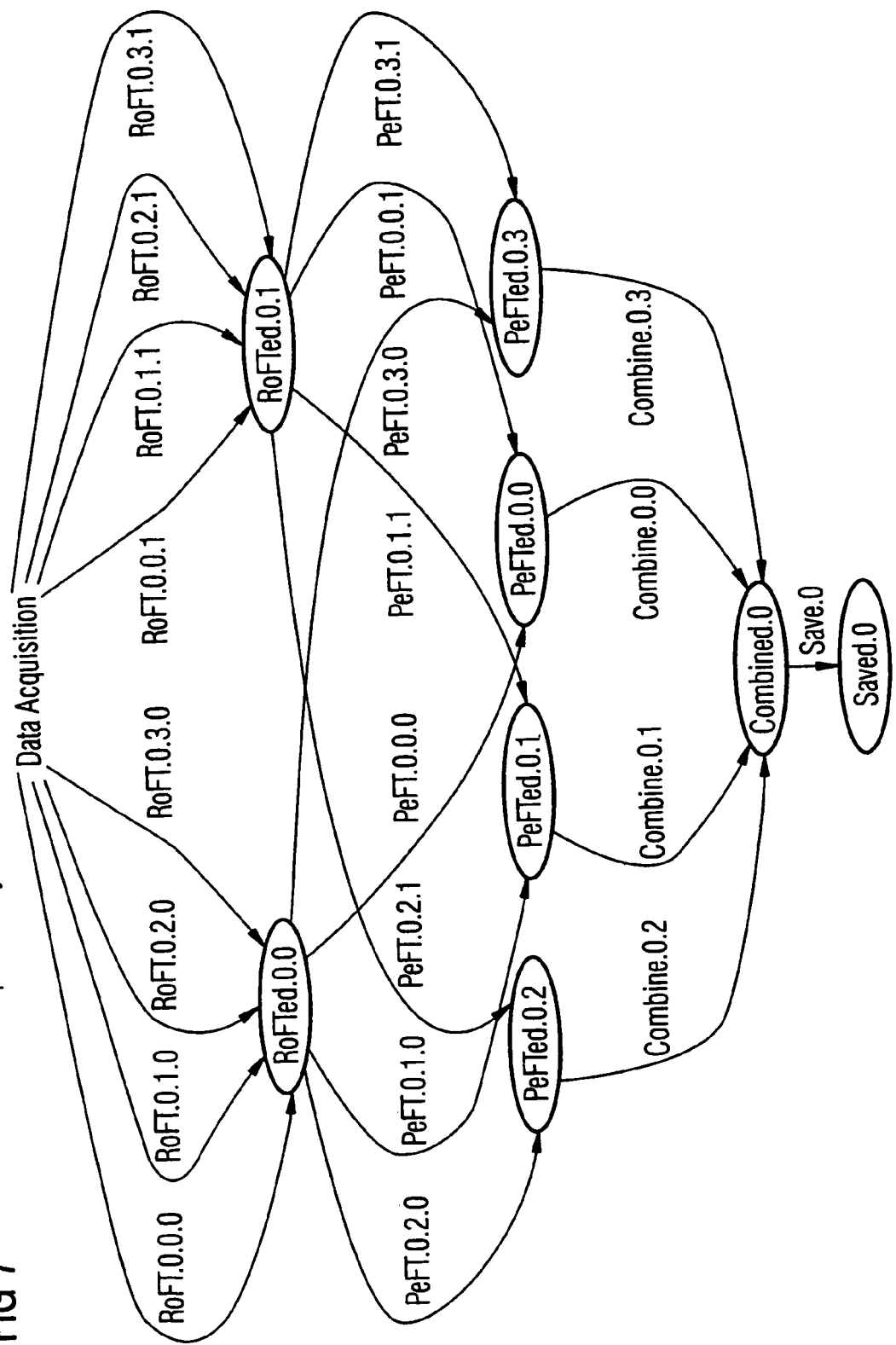
FIG. 7 shows an exemplary representation of an inventive data structure in the form of a dependency tree.

The workflow structure can be represented in a tree-like data structure. FIG. 7 exemplarily shows such a "dependency tree". The links of the tree denote the calculation packets 12-$i$. The nodes denote the respective dependencies or, respectively, the synchronization points.

Specific synchronization points are purely collector points and merely serve for recording of the respectively-executed calculation packet 12-$i$. When this synchronization point is cleared, this denotes that the calculation is finished and the respective slice is stored. This is denoted in FIG. 7 with the lowermost element "Saved.0".

Furthermore, there are specific synchronization points that are purely blockers. This pertains to such synchronization points that are dependent on the acquisition of the data and not on the successful execution of other calculation packets 12-$i$. They can be preset to the state "unblocked", such that their execution begins immediately. The execution of these calculation packets directly depends on the acquired data and is initiated by the data acquisition thread after the data acquisition has occurred. These nodes are denoted with the term "data acquisition" in the exemplary representation in FIG. 7.

Figure 8:
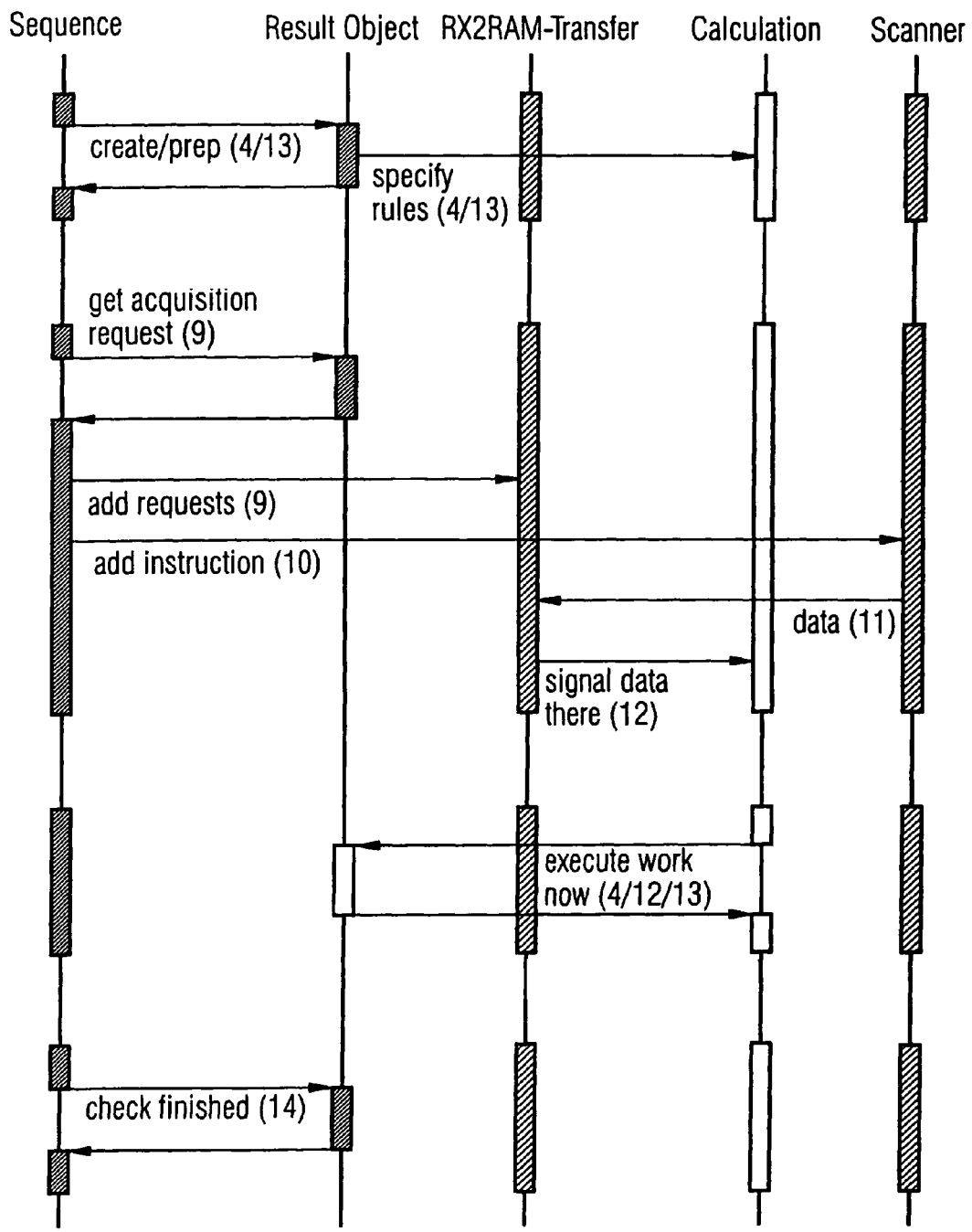
FIG. 8 is an overview representation of a workflow according to another embodiment of the invention.
Figure 9:
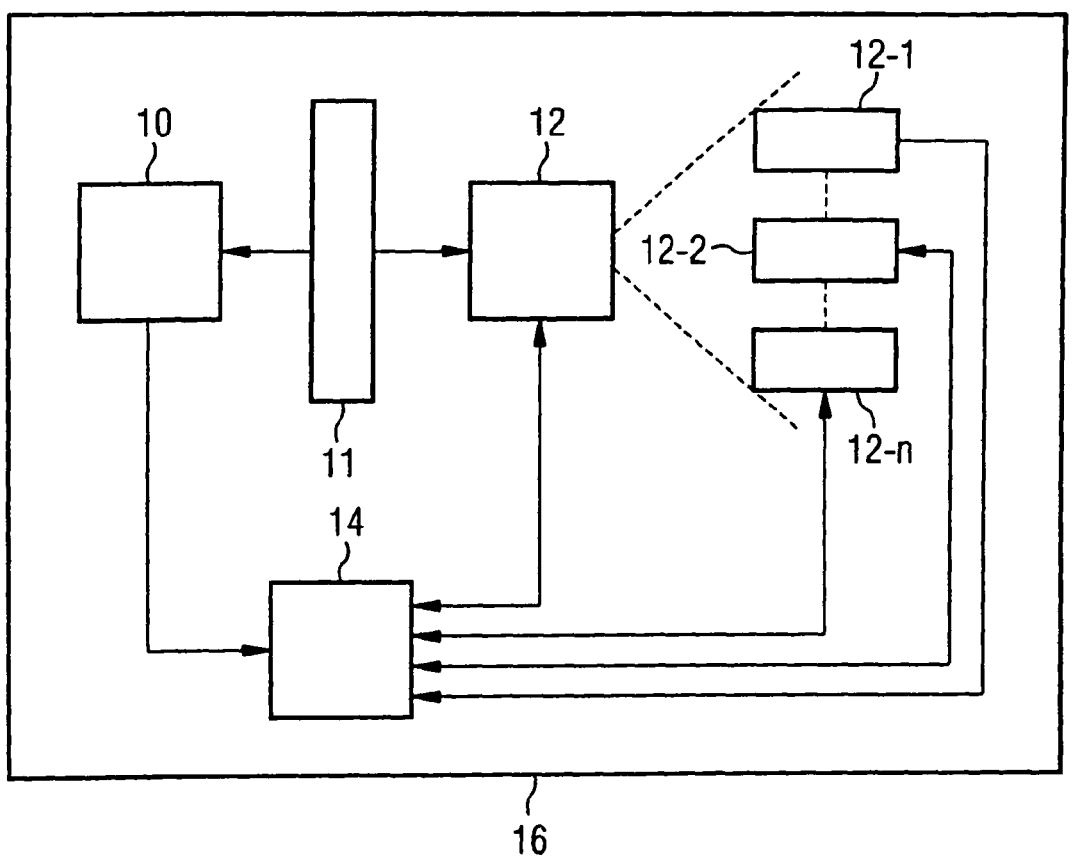
FIG. 9 is an overview representation of the basic units according to a preferred embodiment of the invention.

An example of the inventive synchronization between a sequence or a measurement data sequence and a computation or calculation unit is shown in FIG. 8. Within a preparation or a workflow phase, the sequence can decide whether it would like to generate a specific result object. During the preparation phase, a set of parameterized rules is specified for the result object in order to describe the reconstruction algorithm. The sequence can request measurement data MD after the preparation phase for the result object has concluded.

Since the sequence alone triggers the importation of a specific scan for a result object, it must have information about this result object. For this, an acquisition query is generated for the respective result object. Such a query can contain the following data:
    the scope of the data to be acquired, for example the size of the scan and the number of the channels,
    the target address of the data for each channel,
    a unique identifier for the measured data.

The acquisition query is used in order to form a query at the interface to the scanner of the MR apparatus, such as for the "RX-to-RAM data transfer thread" in order to generate a readout command for the scanner.

After the data have been acquired by the scanner and have been transferred via the interface, the transfer thread informs the calculation unit 12 about the fact that the data have been acquired. It forwards (relays) the unique identifier for these data (which it has received from the result object) to the calculation unit 12. The execution of a data acquisition via the scanner is not a necessary requirement for a result object. Any other calculation processes that have been implemented via the rules can also be executed. The calculation unit 12 is responsible for the organization and execution of the respective calculation packets 12-*i*. In the event that the calculation unit (or calculation therein) 12 "decides" to execute a specific calculation, it invokes a corresponding method for the result object. The actual calculation is entirely encapsulated for the respective user. The calculation unit 12 reads the respective rules.

With the inventive method it is possible to also take into account such calculation processes that are based on measurement data MD that originate from different sources. MR measurements typically acquire input data for different output results, thus for different calculation processes with different data and in a different order. The organization or, respectively, administration and the execution of the calculation lies within the responsibility of the calculation unit 12. The parallelization of the two processes, the implementation of the algorithms and the administration of the storage lies within the range of responsibility of the result object. According to the invention, the restructured and parallelized calculation process is described through parameterized rules.

An advantage of the use of the inventive data structure in the form of dependency trees allows the process of the parallelization to be tested with typical test methods (in particular for convergence on a leaf in the tree, thus to test whether the restructured workflow structure also delivers exactly one result), which is in principle independent of the respectively-used algorithm or, respectively, calculation process. Moreover, it is possible to take suitable measures in the event that an error occurs that, for example, has been caused by a missing or incorrect acquisition of a scan. With the inventive solution it is possible to output a message that specifies which scan is missing for which data set.

By the inventive restructuring of the calculation process into a standardized form it is possible that the method can be applied to any image reconstruction processes and that no conditions whatsoever must be set on the order of the data acquisition. This can increase the flexibility and the stability of the calculation process in an advantageous manner. Due to the restructuring of the calculation process into the inventive workflow structure that comprises the logical dependencies of the respective processes or, respectively, their interdependencies, an external synchronization is no longer necessary.

In an alternative embodiment, the calculation process does not involve the MR image reconstruction but rather (for example) operates on a request of a user for the post-processing of measurement results. This post-processing can be executed according to the same method, such that the post-processing is calculated and run while the data are retrieved from a local storage or a databank.

In a further embodiment, the invention data acquisition is controlled in accordance with the invention. Due to the inventive synchronization between acquisition and calculation process, it is possible that the calculation process already specifies which data must be acquired by the acquisition process. The acquisition process can therewith be controlled directly adapted to the requirements of the calculation process. This development primarily makes sense for such acquisition methods in which the chronological order of the measurement data acquisition has no influence on the image quality (such as, for example, in computed tomography).

In another embodiment of the invention, each calculation packet 12-*i* can be designated with a priority such that the respective calculation packets 12-*i* are given preference with regard to their-priority or only processed after a temporal delay, or even not processed at all.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for computerized optimization of a combined data acquisition and calculation procedure, comprising the steps of:
    acquiring medical image data, selected from the group consisting of magnetic resonance image data, ultrasound image data, and computed tomography image data, in a data acquisition process comprising a plurality of measurement data sequences;
    operating on said medical image data to generate an image from said measurement data by performing an electronic calculation based on the acquired medical image data in an image reconstruction calculation process, while acquiring further medical image data in said data acquisition process in parallel with said calculation process;
    electronically deconstructing said calculation process into a plurality of calculation packets;
    for each of said calculation packets, electronically defining a rule set that designates logical dependencies among all of said calculation packets, said logical dependencies comprising at least one of requirements that must be fulfilled before a calculation packet can be executed, and an amount of said medical image data, represented by one or more of said measurement data sequences, that must be acquired before a calculation packet can be executed;
    dynamically electronically restructuring said calculation process into a workflow structure, based on said calculation packets and said rule sets, in which said acquisition of said measurement data sequences and said calculation packets are interleaved; and
    controlling said acquisition of said medical image data in said measurement data sequences interleaved with said calculation packets in said calculation process using the workflow structure of said calculation process, so that said measurement data sequences are available, as needed, in said workflow structure, and automatically executing the respective calculation packets at respective earliest points in time permitted by the rule set defined therefore.

2. A method as claimed in claim 1 wherein the step of electronically defining a rule set for each calculation packet comprises:
    electronically defining exactly two synchronization points consisting of a blocker that monitors all of said requirements for the execution of the calculation packet and all of said logical dependencies of the calculation packet, and a detector that detects execution of the calculation packet, and wherein the step of automatically executing the respective calculation packet comprises automatically executing the respective calculation packet as soon as said blocker for that calculation packet is not blocked.

3. A method as claimed in claim 1 wherein said data acquisition process proceeds in a sequence and at a speed, and wherein the step of controlling said calculation process comprises controlling said calculation process independently of said sequence and speed of said data acquisition.

4. A method as claimed in claim 1 comprising employing an arbitrary calculation algorithm for executing said calculation process.

5. A method as claimed in claim 1 wherein said calculation process has an associated underlying problem to be solved by said calculation process, and wherein the step of electronically defining a rule set for each calculation packet comprises electronically defining respective rule sets that, in combination, represent a complete description of said problem.

6. A method as claimed in claim 1 comprising electronically dividing said calculation packets among a plurality of threads proceeding in parallel in said calculation process.

7. A method as claimed in claim 1 comprising dividing said data acquisition process into a plurality of threads proceeding in parallel.

8. A method as claimed in claim 1 wherein the step of controlling said calculation process comprises controlling said calculation process in a self-organizing manner with no external synchronization between said data acquisition data process and said calculation process.

9. A method as claimed in claim 1 comprising conducting said calculation process with a computer architecture selected from the group consisting of single processor architectures and multi-processor architectures.

10. A method as claimed in claim 1 comprising executing the steps of deconstructing said calculation process, electronically defining a rule set for each calculation packet, restructuring the calculation process, and controlling the calculation process automatically in a sequence.

11. A method as claimed in claim 1 comprising electronically generating a visual display of said workflow structure in a graphical format selected from the group consisting of a dependency tree and a table.

12. A method as claimed in claim 1 comprising electronically storing intermediate results of at least one of said data acquisition process and said calculation process in a buffer storage, and using the intermediate results in said buffer storage for real-time control of said data acquisition process.

13. A non-transitory computer readable storage medium encoded with programming instructions, said storage medium being loaded into a computerized control and processing system of a medical data acquisition system, said programming instructions causing said computerized control and processing system to:
operate said medical data acquisition system to acquire medical image data, selected from the group consisting of magnetic resonance image data, ultrasound image data, and computed tomography image data, in a data acquisition process comprising a plurality of measurement data sequences;
operate on said medical image data to generate an image from said measurement data by performing an electronic calculation based on the acquired medical image data in an image reconstruction calculation process, while acquiring further medical image data in said data acquisition process in parallel with said calculation process;
electronically deconstruct said calculation process into a plurality of calculation packets;
for each of said calculation packets, electronically define a rule set that designates logical dependencies among all of said calculation packets, said logical dependencies comprising at least one of requirements that must be fulfilled before a calculation packet can be executed, and an amount of said medical image data, represented by one or more of said measurement data sequences, that must be acquired before a calculation packet can be executed;
dynamically electronically restructure said calculation process into a workflow structure, based on said calculation packets and said rule sets, in which said acquisition of said measurement data sequences and said calculation packets are interleaved; and
control said acquisition of said medical image data in said measurement data sequences interleaved with said calculation packets in said calculation process using the workflow structure of said calculation process, so that said measurement data sequences are available, as needed, in said workflow structure, and automatically execute the respective calculation packets at respective earliest points in time permitted by the rule set defined therefore.

14. A non-transitory computer readable storage medium as claimed in claim 13, wherein said programming instructions further cause said computerized control and processing system to:
for each of said calculation packets, identify exactly two synchronization points that define all logical dependencies among said plurality of calculation packets and that, when fulfilled, permit a calculation packet to be executed; and
define a programmed association between each calculation packet and the two synchronization points thereof.

15. A computerized device that optimizes a combined data acquisition and calculation procedure, wherein medical image data, selected from the group consisting of magnetic resonance image data, ultrasound image data, and computed tomography image data, are acquired in a data acquisition process comprising a plurality of measurement data sequences, and wherein the acquired measurement data in the measurement data sequences are operated on by performing an electronic image reconstruction calculation in a calculation process to generate an image from the measurement data while acquiring further measurement data in the data acquisition process in parallel with the calculation process, said device comprising:
a processor configured to electronically deconstruct said calculation process into a plurality of calculation packets;
said processor being configured, for each of said calculation packets, to electronically define a rule set that designates logical dependencies among all of said calculation packets, said logical dependencies comprising at least one of requirements that must be fulfilled before a calculation packet can be executed, and an amount of said medical image data represented by one or more of said measurement data sequences, that must be acquired before a calculation packet can be executed;
said processor being configured to dynamically electronically restructure said calculation process into a workflow structure, based on said calculation packets and said rule sets, in which said acquisition of said measurement data sequences and said calculation packets are interleaved; and a control unit in communication with said processor, said control unit being configured to control said acquisition of said medical image data in said measurement data sequences interleaved with said calculation packets in said calculation process using the workflow structure of said calculation process, so that said measurement data sequences are available, as needed, in said workflow structure, and said processor being configured to automatically execute the respective calculation packets at respective earliest points in time permitted by the rule set defined therefore.

* * * * *